United States Patent
Momose et al.

(10) Patent No.: US 10,371,658 B2
(45) Date of Patent: Aug. 6, 2019

(54) GAS SENSOR AND SENSOR APPARATUS

(71) Applicant: FUJITSU LIMITED, Kawasaki-shi, Kanagawa (JP)

(72) Inventors: Satoru Momose, Atsugi (JP); Osamu Tsuboi, Kawasaki (JP); Kazuaki Karasawa, Hadano (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 15/682,867

(22) Filed: Aug. 22, 2017

(65) Prior Publication Data

US 2017/0350839 A1 Dec. 7, 2017

Related U.S. Application Data

(63) Continuation of application No. PCT/JP2015/056925, filed on Mar. 10, 2015.

(51) Int. Cl.
*G01N 27/414* (2006.01)
*G01N 27/12* (2006.01)

(52) U.S. Cl.
CPC ......... *G01N 27/12* (2013.01); *G01N 27/4141* (2013.01)

(58) Field of Classification Search
CPC ... G01N 27/12; G01N 27/129; G01N 27/4141
See application file for complete search history.

(56) References Cited

U.S. PATENT DOCUMENTS

| 5,072,262 A | 12/1991 | Uekita | |
|---|---|---|---|
| 2001/0032493 A1* | 10/2001 | Samman | G01N 27/129 73/31.06 |
| 2002/0020853 A1* | 2/2002 | Nakashima | G01N 27/129 257/199 |

(Continued)

FOREIGN PATENT DOCUMENTS

| JP | S63-000124 A | 1/1988 |
|---|---|---|
| JP | 2002-031619 A1 | 1/2002 |

(Continued)

OTHER PUBLICATIONS

Lauque, et al., "Highly sensitive and selective room temperature NH3 gas microsensor using an ionic conductor (CuBr) film," May 25, 2004, Analytica Chimica Acta 515 (2004) pp. 279-284. (Year: 2004).*

(Continued)

*Primary Examiner* — Matthew C Landau
*Assistant Examiner* — Mark Hatzilambrou
(74) *Attorney, Agent, or Firm* — Kratz, Quintos & Hanson, LLP

(57) ABSTRACT

A gas sensor includes a p-type semiconductor layer that contains copper or silver cations and contacts with detection target gas, a first electrode that is a Schottky electrode to the p-type semiconductor layer, a high-resistance layer that is provided between the p-type semiconductor layer and the first electrode such that the p-type semiconductor layer and the first electrode partly contact with each other and has resistance higher than that of each of the p-type semiconductor layer and the first electrode, and a second electrode that is an ohmic electrode to the p-type semiconductor layer.

9 Claims, 23 Drawing Sheets

(56) References Cited

U.S. PATENT DOCUMENTS

2008/0185616 A1* 8/2008 Johnson .............. G01N 27/129
257/253
2011/0263036 A1 10/2011 Blauw
2012/0090381 A1* 4/2012 Andersson .......... G01N 27/129
73/31.06

FOREIGN PATENT DOCUMENTS

| JP | 2003-315299 A1 | 11/2003 |
| JP | 2009-042213 A1 | 2/2009 |
| JP | 2011-203256 A1 | 10/2011 |

OTHER PUBLICATIONS

P. Lauque, et al.; "Electrical Properties of Thin-films of the Mixed Ionic-electronic Conductor CuBr: Influence of Electrode Metals and Gaseous Ammonia;" Journal of the European Ceramic Society; vol. 19; 1999; pp. 823-826 (4 Sheets)/Cited in International Search Report.
International Search Report for International Application No. PCT/JP2015/056925 dated May 12, 2015.
Office Action in Chinese Application No. 201580077528, dated Jan. 25, 2019, including English translation.

* cited by examiner

GAS SENSOR AND SENSOR APPARATUS

CROSS-REFERENCE TO RELATED APPLICATION

This application is a continuation application of International Application PCT/JP2015/056925 filed on Mar. 10, 2015 and designated the U.S., the entire contents of which are incorporated herein by reference.

FIELD

The embodiments discussed herein are related to a gas sensor and a sensor apparatus.

BACKGROUND

Conventionally, a gas sensor detects gas from variation of current arising from contact of a sensitive film, for which, for example, tin dioxide or the like is used, and gas with each other.

In such a gas sensor as just described, since current is supplied using a constant current power supply, power consumption is high. Further, since the gas sensor is heated to a temperature at which a good detection characteristic is obtained, much power is consumed by a heater for heating the gas sensor.

Thus, also a gas sensor is available which detects gas based on a potential difference arising from absorption of gas. For example, in such a gas sensor as just described, an electrode having reactivity with respect to detection target gas and an electrode that is inactive to the detection target gas are provided on the opposite faces of a solid electrolyte layer such that gas is detected based on a potential difference generated as a result of chemical reaction occurring by the contact with gas.

SUMMARY

The present gas sensor includes a p-type semiconductor layer that contains copper or silver cations and contacts with detection target gas, a first electrode that is a Schottky electrode to the p-type semiconductor layer, a high-resistance layer that is provided between the p-type semiconductor layer and the first electrode such that the p-type semiconductor layer and the first electrode partly contact with each other and has resistance higher than that of each of the p-type semiconductor layer and the first electrode, and a second electrode that is an ohmic electrode to the p-type semiconductor layer.

The object and advantages of the invention will be realized and attained by means of the elements and combinations particularly pointed out in the claims. It is to be understood that both the foregoing general description and the following detailed description are exemplary and explanatory and are not restrictive of the invention.

DESCRIPTION OF EMBODIMENTS

However, with a gas sensor that detects gas based on the potential difference, it is difficult to obtain good sensitivity.

Therefore, it is desired to implement a gas sensor in which the power consumption is low and by which good sensitivity can be obtained.

In the following, a gas sensor and a sensor apparatus according to an embodiment are described with reference to FIGS. 1 to 9 of the drawings.

The gas sensor according to the present embodiment is a gas sensor that detects a chemical substance in gas, especially, a gas sensor that detects a chemical substance in the atmosphere. For example, the gas sensor is preferably applied to a gas sensor that detects a very small amount of a chemical substance within expiration.

The gas sensor of the present embodiment is a gas sensor that detects gas based on a potential difference arising from absorption of gas at a temperature around a room temperature. Therefore, the power consumption is low.

Figure 1:
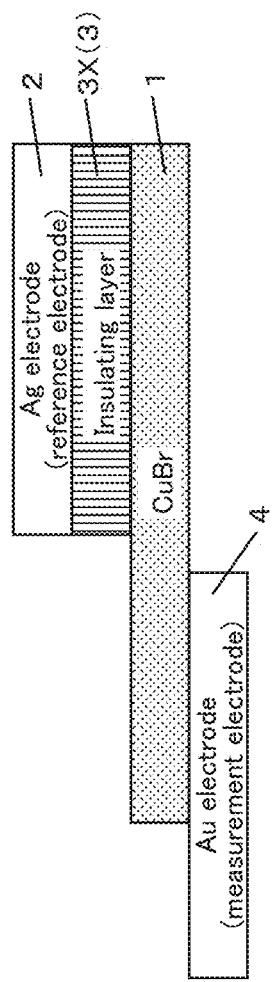
FIG. 1 is a schematic view depicting a configuration of a gas sensor according to an embodiment.

Further, as depicted in FIG. 1, the gas sensor of the present embodiment includes a p-type semiconductor layer 1 that contains copper or silver cations and contacts with detection target gas, a first electrode 2 that serves as a Schottky electrode to the p-type semiconductor layer 1, a high-resistance layer 3 that is provided between the p-type semiconductor layer 1 and the first electrode 2 such that the p-type semiconductor layer 1 and the first electrode 2 partly contact with each other and has resistance higher than those of the p-type semiconductor layer 1 and the first electrode 2, and a second electrode that serves as an ohmic electrode to the p-type semiconductor layer 1. Therefore, good sensitivity is obtained with the gas sensor that detects gas based on a potential difference.

It is to be noted that the gas sensor that includes the p-type semiconductor layer 1, first electrode 2, high-resistance layer 3 and second electrode 4 is also called gas sensor device. It is to be noted that the detection target gas is also called observation target gas.

Here, the p-type semiconductor layer 1 is formed from a p-type semiconductor material that is a compound containing copper or silver cations.

For example, as the p-type semiconductor material, it is preferable to use cuprous bromide (cooper (I) bromide; CuBr) that exhibits a sharp response to ammonia where the detection target gas is ammonia. It is to be noted that an example of a response of cuprous bromide to ammonia is indicated in the form of a significant variation of the electric resistance at a room temperature, for example, in Pascal Lauque et al., "Highly sensitive and selective room temperature NH3 gas microsensor using an ionic conductor (CuBr) film", Analytica Chimica Acta, Vol. 515, pp. 279-284 (2004), the entire content of which is incorporated herein by reference (hereinafter referred to as technical literature).

Since also a p-type semiconductor material such as cuprous oxide (cooper (I) oxide; $Cu_2O$) that is a copper compound, silver bromide (AgBr) or silver sulfide ($Ag_2O$) that is a silver compound indicates a reaction to ammonia by a similar mechanism, the materials just described can be used similarly to cuprous bromide.

In this manner, preferably the p-type semiconductor layer 1 contains one selected from a group including cuprous bromide, cuprous oxide, silver bromide and silver sulfide.

Especially, where a semiconductor that is a copper or silver compound is used as the p-type semiconductor that contacts with detection target gas, a gas sensor that has a high coordination performance to ions of copper or silver and selectively detects ammonia or amine can be configured.

Further, as the internal resistance of the device decreases, decrease of the potential difference by outflow of charge becomes more likely to occur, and therefore, it is advantageous to increase the internal resistance of the device.

Therefore, it is an effective to provide a Schottky barrier between the p-type semiconductor layer and one of the electrodes by using a p-type semiconductor material whose work function is higher than that of one of the electrode materials.

Therefore, in the present embodiment, the Schottky barrier is formed between the first electrode 2 and the p-type semiconductor layer 1 by setting the work function of a metal material configuring the first electrode 2 lower than that of a material configuring the p-type semiconductor layer 1 such that the first electrode 2 serves as a Schottky electrode to the p-type semiconductor layer 1.

On the other hand, the second electrode 4 and the p-type semiconductor layer 1 are ohmic-coupled to each other by setting the work function of a metal material configuring the second electrode 4 equal to or higher than that of a material configuring the p-type semiconductor layer 1 such that the second electrode 4 serves as an ohmic electrode to the p-type semiconductor layer 1.

In particular, the first electrode 2 is formed from a material that serves as a Schottky electrode to the p-type semiconductor layer 1, and the second electrode 4 is formed from a material that serves as an ohmic electrode to the p-type semiconductor layer 1.

In this case, the work function of the metal material configuring the first electrode 2 is lower than those of the metal material configuring the second electrode 4 and the material configuring the p-type semiconductor layer 1.

For example, the metal material configuring the first electrode 2 is silver (Ag), and the metal material configuring the second electrode 4 is gold (Au). It is to be noted that the first electrode 2 is also called reference electrode. Further, the second electrode 4 is also called measurement electrode or detection electrode.

Further, in order to increase the resistance between the p-type semiconductor layer 1 and the first electrode 2 to increase the potential difference between the first electrode 2 and the second electrode 4, the high-resistance layer 3 formed from a material having a resistivity higher than those of the p-type semiconductor layer 1 and the first electrode 2 is provided between the p-type semiconductor layer 1 and the first electrode 2. Here, the high-resistance layer 3 is an insulating layer formed from an insulating material (material having an insulating property).

Good sensitivity can be obtained by providing the high-resistance layer 3 such that the first electrode 2 side of the p-type semiconductor layer 1 has higher resistance to movement of charge (negative charge) than that of the second electrode 4 side of the p-type semiconductor layer 1 in this manner. In particular, good sensitivity can be obtained by configuring the coupling between the p-type semiconductor layer 1 and the first electrode 2 so as to have higher resistance to movement of charge (negative charge) than that of the coupling between the p-type semiconductor layer 1 and the second electrode 4. In this case, the high-resistance layer 3 has resistance higher than that of the second electrode 4. In other words, the high-resistance layer 3 is formed from a material having resistivity higher than that of the second electrode 4.

Especially, the high-resistance layer 3 is provided between the p-type semiconductor layer 1 and the first electrode 2 such that the p-type semiconductor layer 1 and the first electrode 2 partly contact with each other. Here, although the high-resistance layer 3 is provided between the p-type semiconductor layer 1 and the first electrode 2, since the high-resistance layer 3 has defects 3A (refer to FIGS. 4, 7 and 8) and exists intermittently, the p-type semiconductor layer 1 and the first electrode 2 directly contact with each other at portions thereof. In particular, in the coupling region between the p-type semiconductor layer 1 and the first electrode 2, locations at which the p-type semiconductor layer 1 and the first electrode 2 directly contact with each other and locations at which the high-resistance layer 3 exists between the p-type semiconductor layer 1 and the first electrode 2 exist in a mixed manner. Therefore, the high-resistance layer 3 is provided between the p-type semiconductor layer and the first electrode 2 such that the p-type semiconductor layer 1 and the first electrode 2 partly contact with each other. The high-resistance layer 3 having such defects A3 as described above can be formed by increasing the surface roughness of the p-type semiconductor layer 1 that serves as an underlying layer as hereinafter described. In other words, the high-resistance layer 3 having such defects 3A as described above can be formed by forming a thin high-resistance layer 3 on the p-type semiconductor layer 1 having a high surface roughness. In this case, the p-type semiconductor layer 1 and the first electrode 2 are coupled to each other such that capacitors and Schottky junctions are parallel.

Further, the high-resistance layer 3 is partly provided at one side (here, at the upper side) of the p-type semiconductor layer 1, and the first electrode 2 is provided on the high-resistance layer 3. In short, the first electrode 2 contacts with the high-resistance layer 3 and the high-resistance layer 3 contacts with the one side of the p-type semiconductor layer 1. Consequently, the surface of the p-type semiconductor layer 1 is partly exposed so as to contact with the detection target gas. On the other hand, the second electrode 4 is provided at the other side (here, at the lower side) of the p-type semiconductor layer 1. In short, the second electrode 4 contacts with the surface of the other side of the p-type semiconductor layer 1.

In this manner, the first electrode 2 is coupled to the p-type semiconductor layer 1 through the high-resistance layer 3 having the defects 3A. In other words, the high-resistance layer 3 having the defects 3A is provided between the first electrode 2 and the p-type semiconductor layer 1. Consequently, the p-type semiconductor layer 1 and the first electrode 2 are coupled to each other such that the capacitors and Schottky junctions are parallel. On the other hand, the second electrode 4 is directly coupled to the p-type semiconductor layer 1. Consequently, good sensitivity is obtained.

Further, as hereinafter described, where the p-type semiconductor layer 1 is processed so as to decrease the hole density thereof, for example, by contact with reducing gas, if reducing detection target gas contacts with the p-type semiconductor layer 1, then the potential of the second electrode 4 varies in the positive direction. Consequently, since the moving direction of the potential upon operation reverses, the time (return time) required for restoration of a detection portion to an initial state after detection operation of the detection target gas can be decreased.

Figure 2:
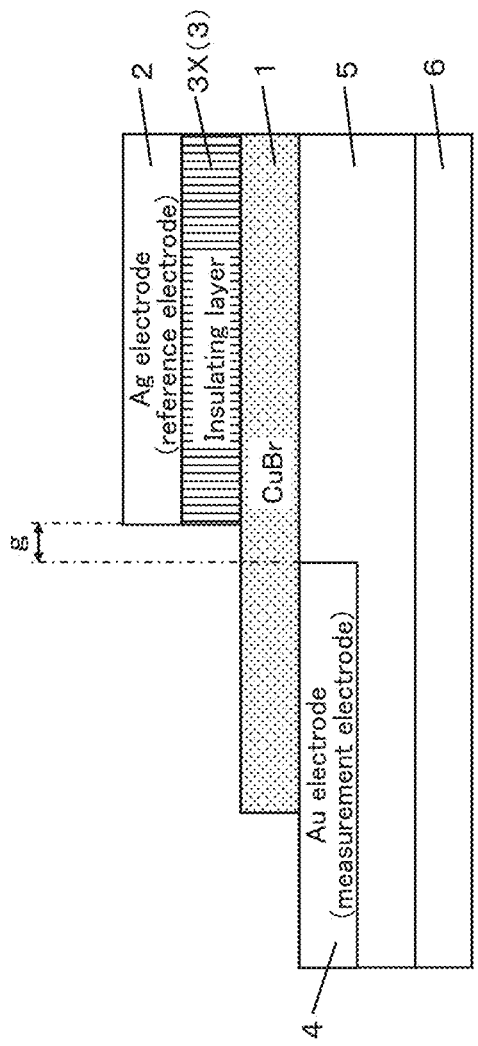
FIG. 2 is a schematic sectional view depicting an example of a configuration of the gas sensor according to the embodiment.

In particular, as depicted in FIG. 2, the gas sensor (sensor device) may be configured such that a gold electrode (Au electrode) as the second electrode (measurement electrode) 4 is provided on the silicon substrate 6 having an $SiO_2$ film 5 and a cuprous bromide layer (CuBr layer) as the p-type semiconductor layer 1 is provided on the second electrode 4 and besides a lithium fluoride layer (LiF layer) having the defects 3A is provided as the high-resistance layer 3 (insulating layer 3X) having the defects 3A on the p-type semiconductor layer 1 and a silver electrode (Ag electrode) as the first electrode 2 is provided on the high-resistance layer 3.

It is to be noted that, while the high-resistance layer 3 here is the insulating film 3X formed from an insulating material, the high-resistance layer 3 is not limited to this. Further, the first electrode 2 and the second electrode 4 here are provided in a displaced relationship in an in-plane direction such that a gap g is formed between the first electrode 2 and the second electrode 4.

Figure 3:
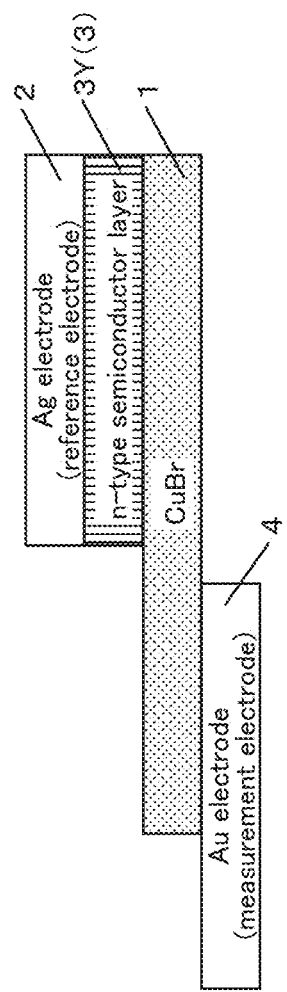
FIG. 3 is a schematic sectional view depicting a configuration of a modification to the gas sensor according to the embodiment.

For example, as depicted in FIG. 3, the high-resistance layer 3 may be an n-type semiconductor layer 3Y having a work function lower than those of the p-type semiconductor layer 1 and the first electrode 2. In other words, the material having a resistivity higher than those of the p-type semiconductor layer 1 and the first electrode 2 may be formed from an n-type semiconductor material indicating a work function lower than those of the p-type semiconductor layer 1 and the first electrode 2 such that the high-resistance layer 3 is configured from the n-type semiconductor layer 3Y formed from the n-type semiconductor material.

It is to be noted that, even if the high-resistance layer 3 is the insulating layer 3X formed from an insulating material or is the n-type semiconductor layer 3Y having a work function lower than those of the p-type semiconductor layer 1 and the first electrode 2, the high-resistance layer 3 has high resistance with respect to movement of charge (negative charge) and suppresses movement of charge (negative charge). Therefore, the high-resistance layer is also called charge movement suppression layer (negative charge movement suppression layer).

In this manner, if the high-resistance layer 3 is configured as the n-type semiconductor layer 3Y and the work function of a material configuring the n-type semiconductor layer 3Y is lower than those of a material configuring the p-type semiconductor layer 1 adjacent to the n-type semiconductor layer 3Y and a material configuring the first electrode 2, then movement of negative charge from the material configuring the p-type semiconductor layer 1 to the metal material configuring the first electrode 2 is difficult. Therefore, similar operation is exhibited to that where the insulating layer 3X formed from an insulating material is used for the high-resistance layer 3.

However, if an n-type semiconductor material contacts with a p-type semiconductor material, then generally a depletion layer is formed on the surfaces of the materials by supplying electrons to the p-type semiconductor material. In the present embodiment, since gas molecules are adsorbed to the surface of the p-type semiconductor layer 1 and movement of electrons is performed with the p-type semiconductor layer 1, the carrier concentration in the inside of the p-type semiconductor layer 1 varies together with detection operation. Since also the thickness of the depletion layer varies together with the variation of the carrier concentration, also the resistance value sandwiching the n-type semiconductor layer 3Y varies significantly.

Therefore, in order to form a depletion layer in the inside of the p-type semiconductor layer 1, where the n-type semiconductor material used here exhibits an insufficient carrier concentration, it is easier to handle becomes the operation is simple. Here, a group of materials having an n-type conductivity and having a low carrier concentration are used for an electron transport layer of an electroluminescence (EL) device and are called electron transport material.

Where an electron transport layer for which such an electron transport material is used is used as the n-type semiconductor layer 3Y, if the work function of the electron transport layer 3Y is lower than that of the p-type semiconductor layer 1, then the electron transport layer 3Y functions as a simple insulating layer. Therefore, electrical operation of the inside of the p-type semiconductor layer 1 is similar to that where the insulating layer 3X for which an insulating material is used is used.

On the other hand, if the work function of the electron transport layer 3Y is equal to or higher than that of the first electrode 2, then since the first electrode 2 and the electron transport layer 3Y are ohmic-coupled to each other, the thickness of a region that acts as the insulating layer is reduced and movement of charge between the p-type semiconductor layer 1 and the first electrode 2 is facilitated. Accordingly, also where the electron transport layer 3Y for which an electron transport material is used is used, a configuration is applied such that the work function of the electron transport layer 3Y is lower than that of the first electrode 2.

For example, if the material configuring the first electrode 2, the material configuring the second electrode 4 and the material configuring the p-type semiconductor layer 1 are silver, gold and cuprous bromide, respectively, then bathocuproin whose work function is approximately 3.5 eV is suitable as an electron transport material configuring the electron transport layer (n-type semiconductor layer) 3Y as the high-resistance layer 3 because bathocuproin can increase the difference in work function and can improve the sensitivity further. Similarly, also such electron transport materials as various phenanthroline derivatives, various oxadiazole derivatives, various triazole derivatives and tris (8-quinolinolato) aluminum can be used as the electron transport material configuring the electron transport layer 3Y as the high-resistance layer 3.

Further, it is preferable for the first electrode 2 and the second electrode 4 to contain a metal material having an ionization tendency lower than that of a metal element contained in the p-type semiconductor layer 1. In particular, it is preferable to form the first electrode 2 and the second electrode 4 from a metal material nobler than a metal element contained in the p-type semiconductor layer 1. This makes it possible to improve the durability.

It is to be noted that, since a solid electrolyte practically used in a conventional gas sensor that detects gas on the basis of a potential difference indicates a sufficient ion conductivity at a temperature as high as approximately 500° C., it is heated by a heater, and this significantly increases the power consumption of the heater. Further, the heater is not only used for the electric characteristic of a device but also used for facilitation of desorption of gas molecules adsorbed to a detection body to reduce the time required for restoration of a detection location. However, the power consumption of the heater used for such an object as described above restricts usage of the gas sensor.

On the other hand, by using the p-type semiconductor layer 1 containing copper or silver cations as described above and configuring the gas sensor as described above, a potential difference detection gas sensor in which good detection sensitivity is obtained in operation at a room temperature (low-temperature operation) and the power consumption is low and besides also restoration operation of the detection location is performed at a high speed can be implemented. Consequently, a heater used in a conventional gas sensor may not be provided and applications of the gas sensor can be increased.

Especially, since a method for measuring the potential difference appearing in the inside of the device by contact with gas (namely, potential difference between the first electrode 2 and the second electrode 4) is adopted, current supply from the outside is not required, which is advantageous in power saving. Further, by performing a process for decreasing the hole density in the p-type semiconductor layer 1, for example, through contact with reducing gas as hereinafter described, it is possible to cause the potential of the second electrode 4 to vary in the positive direction if reducing detection target gas contacts with the p-type semiconductor layer 1. Consequently, the direction in which the potential moves upon operation can be reversed and the time (return time) required for restoration of the detection location to an initial state after detection operation of the detection target gas can be reduced, and the speed of the restoration operation of the detection portion, namely, the recovery speed of the potential difference, can be increased. In this manner, a gas sensor that has high sensitivity and is reduced in time required for recovery to an initial state can be implemented. Further, since potential difference spontaneously occurring as a result of increase in doping of electrons from gas molecules into the p-type semiconductor layer 1 and in electric field directly arising from the doping is used as hereinafter described, the device need not be heated and measurement can be performed with good detection sensitivity using a simple circuit that exhibits low power consumption.

In the following, operation of the gas sensor configured as described above where the material of the p-type semiconductor layer 1 is cuprous bromide (CuBr); the observation target gas is ammonia; the material of the first electrode 2 is silver (Ag); the material of the second electrode 4 is gold; and the high-resistance layer 3 having the defects 3A is the insulating layer 3X (refer to FIGS. 1 and 2) is described below.

It is to be noted that, if a CuBr layer is formed by a method disclosed in the technical literature described above, then where gold (work function of approximately 5.1 eV) is used for the electrode, the electrode serves as an ohmic electrode to CuBr, but where silver (work function of approximately 4.3 eV) having a lower work function is used for the electrode, the electrode serves as a Schottky electrode to CuBr.

The insulating layer 3X as the high-resistance layer 3 is formed on the surface obtained by increasing the surface roughness of the CuBr layer that is the p-type semiconductor layer 1, for example, using a vacuum deposition method such that an average thickness is several nm (for example, 10 nm or less). Consequently, the insulating layer 3X as the high-resistance layer 3 provided between the CuBr layer that is the p-type semiconductor layer 1 and a silver electrode as the first electrode 2 that is the Schottky electrode is formed so as to have fine detects 3A (namely, such that the insulating layer 3X exists intermittently), and a state in which the CuBr layer 1 and the silver electrode 2 directly contact with each other through the fine defects 3A can be implemented.

Here, as means for increasing the surface roughness of the CuBr layer 1, a method is available by which, for example, the surface of the CuBr layer 1 is exposed to vapor of a substance that dissolves CuBr to some degree thereby to reconfigure the surface of the CuBr layer 1. In particular, a simple method may be used by which the CuBr layer 1 is exposed to the atmosphere so as to be exposed to water vapor in the air.

By providing the insulating layer 3X having such fine defects 3A as described above between the CuBr layer 1 and the silver electrode 2, a capacitance that is not too high is provided in a region in which the CuBr layer 1 and the silver electrode 2 are coupled to each other and the CuBr layer 1 and the silver electrode 2 are Schottky-coupled to each other with high resistance. In other words, the p-type semiconductor layer 1 and the first electrode 2 are coupled to each other such that the capacitors and the Schottky junctions are parallel. Consequently, a high-sensitivity potential difference detection type gas sensor is implemented.

Further, by performing a process for adjusting the carrier concentration (hole density) in the inside of the CuBr layer 1 in the gas sensor having such a configuration as described above, the recovery speed of the potential difference after contact with observation target gas comes to an end can be increased remarkably.

An operation mechanism of the gas sensor having such a configuration as described above is described with reference to FIGS. 4 to 8.

Figure 4:
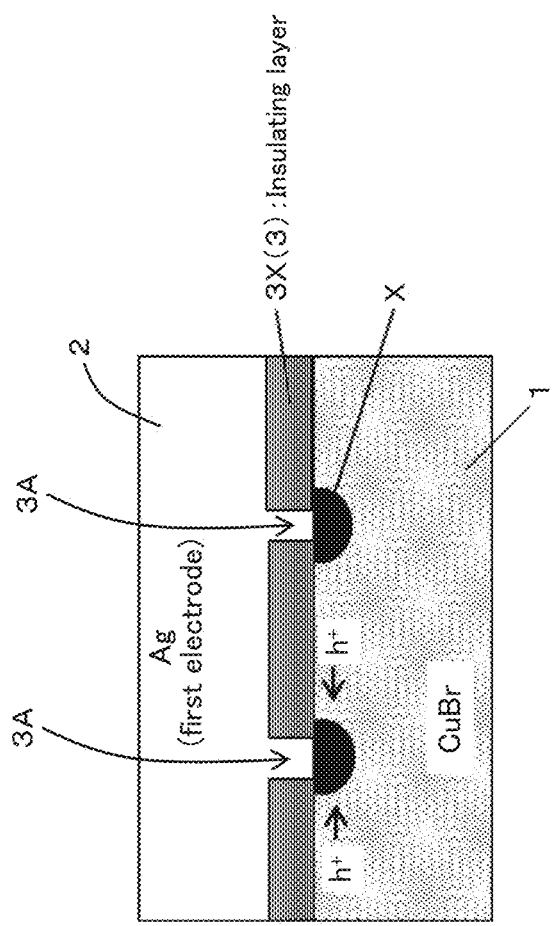
FIG. 4 is a schematic sectional view depicting a state that is a premise of operation of the gas sensor according to the embodiment.

As depicted in FIG. 4, if the defects 3A exist in the insulating layer 3X provided between the CuBr layer 1 and the silver electrode 2 and regions (fine regions; Schottky junction regions) exist in which the CuBr layer 1 and the silver electrode 2 directly contact with each other through the defects 3A, then at the side of the CuBr layer 1 in the region, electrons are injected from the surface of silver having a lower work function into CuBr that is a p-type semiconductor. As a result, a depletion layer X in which the carrier density is very low is formed in the CuBr layer 1. It is to be noted, in FIG. 4, a region that originally serves as a depletion layer is depicted as the depletion layer X.

However, where the thickness of the depletion layer X is equal to or greater than the width of the region in which the CuBr layer 1 and the silver electrode 2 directly contact with each other, electrons injected from the silver electrode 2 are diffused to the CuBr layer 1 in regions in which the insulating layer 3X contacts around the regions in which the CuBr layer 1 and the silver electrode 2 directly contact with each other and holes can move to the regions, in which the CuBr layer 1 and the silver electrode 2 directly contact with each other, from the peripheral CuBr layer 1 around the regions.

As such a result of such carrier movement, capacitors across the insulating layer 3X are formed and a stabilized state can be formed in the form different from that of a depletion layer formed normally.

Figure 5:
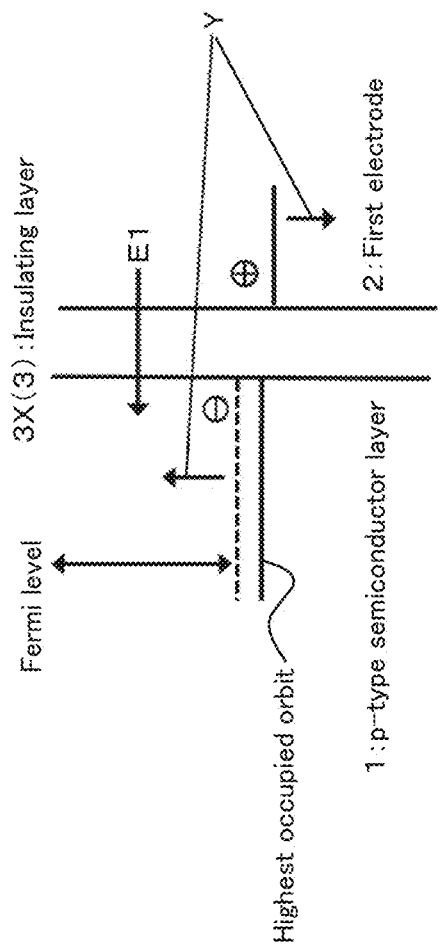
FIG. 5 is a view depicting an energy state at a location at which an insulating layer exists between a first electrode and a p-type semiconductor layer in the gas sensor according to the embodiment.
Figure 7:
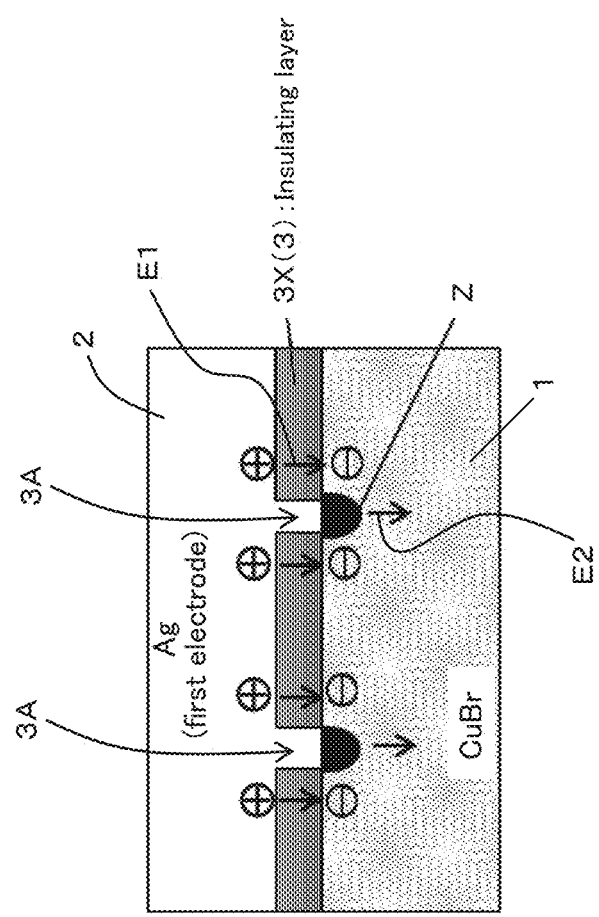
FIG. 7 is a schematic sectional view depicting an initial state of the gas sensor according to the embodiment.

In particular, as depicted in FIGS. 5 and 7, the Fermi level in the inside of the silver electrode 2 and the CuBr layer 1 is moved by charge accumulated in each capacitor region, and, in the capacitor region across the insulating layer 3X, a local electric field E1 from the silver electrode 2 toward the CuBr layer 1 is formed. It is to be noted that, in FIG. 5, an arrow mark denoted by reference character Y indicates that the level is moved by accumulated charge.

Figure 6:
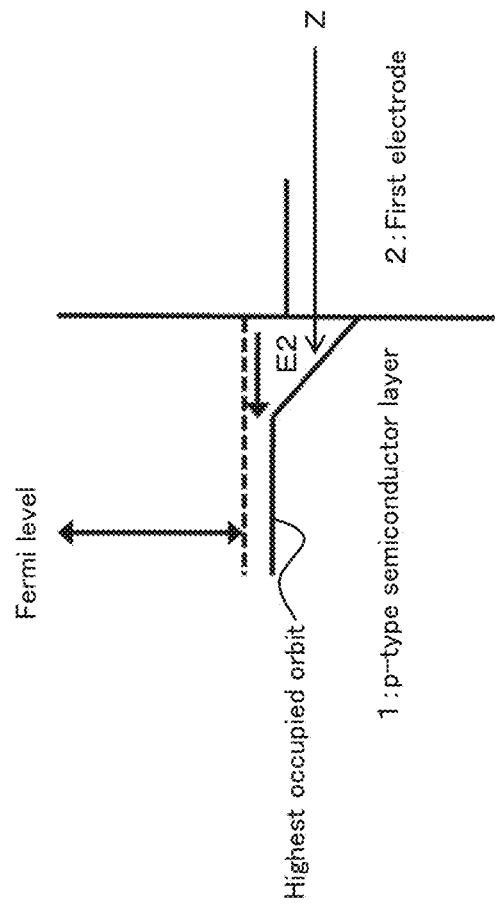
FIG. 6 is a view depicting an energy state of a region in which the first electrode and the p-type semiconductor layer directly contact with each other in the gas sensor according to the embodiment.

On the other hand, in the region in which the silver electrode 2 and the CuBr layer 1 directly contact with each other, movement of electrons from the silver electrode 2 to the CuBr layer 1 is constrained by the potential difference generated by formation of the capacitor, and therefore, the number of electrons existing in the region that serves as a depletion layer in a normal case becomes insufficient for the cancellation of the internal electric field. Therefore, as depicted in FIGS. 6 and 7, an electric field E2 in a direction toward the inside of the CuBr layer 1 from the region is formed. It is to be noted that, in FIGS. 6 and 7, reference character Z depicts a depletion layer in which electrons are partly lost.

If air containing, for example, ammonia is contacted with the CuBr layer 1 exposed to the external air of the gas sensor in such a state as described above, then ammonia molecules are adsorbed to the surface of the exposed CuBr layer 1 and electrons are doped from the ammonia molecules into CuBr.

Then, when electrons are doped, the hole density in the inside of the CuBr layer 1 decreases and holes become insufficient in the CuBr layer 1 in the region in which the CuBr layer 1 and the silver electrode 2 directly contact with each other. Therefore, holes are further collected from the surrounding portion of the CuBr layer 1.

Figure 8:
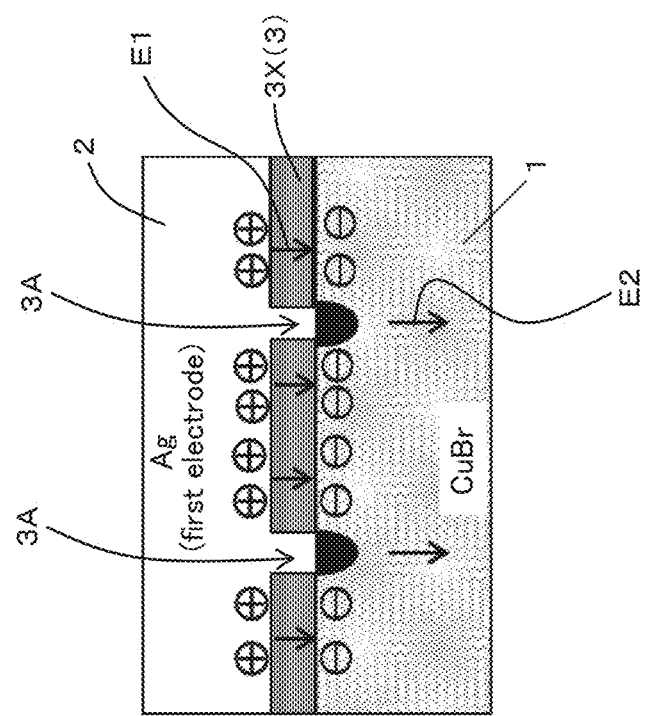
FIG. 8 is a schematic sectional view depicting a state in which a gas detection operation by the gas sensor according to the embodiment is performed.

At this time, while, in each region in which a capacitor is formed, the electric field does not leak to the outside by the existence of paired charge, in the CuBr layer 1 in the region in which it directly contacts with the silver electrode 2, the electric field E2 toward the inside of the CuBr layer 1 increases corresponding to increase of holes as depicted in FIG. 8.

Therefore, the potential in the inside of the CuBr layer 1 increases by absorption of ammonia molecules. Here, since the variation amount of the potential increases in proportion to the variation amount of the electric field toward the inside of the CuBr layer 1, namely, in proportion to the surplus amount of holes existing in the CuBr layer 1 of the region, in which the CuBr layer 1 and the silver electrode 2 directly contact with each other, with respect to electrons, the variation amount of the potential increases in proportion to the number of electrons doped into the CuBr layer 1, namely, the number of ammonia molecules adsorbed to the surface of the CuBr layer 1 (namely, the ammonia concentration in the air).

If the potential in the inside of the CuBr layer 1 increases, then the potential of the silver electrode 2 as the first electrode and the potential of the gold electrode 4 as the second electrode decrease relatively. Then, a potential difference appears between the silver electrode 2 as the first electrode (reference electrode) and the gold electrode 4 as the second electrode (measurement electrode; detection electrode). In this case, if a process for decreasing the hole density in the CuBr layer 1 hereinafter described is not performed, then the potential of the gold electrode 4 as the second electrode becomes lower than the potential of the silver electrode 2 as the first electrode. On the other hand, if a process for decreasing the hole density in the CuBr layer 1 hereinafter described is performed, then the potential of the gold electrode 4 as the second electrode becomes higher than the potential of the silver electrode 2 as the first electrode.

The concentration of observation target gas can be measured by measuring the potential difference between the first electrode 2 as the reference electrode and the second electrode 4 as the detection electrode by the principle described above.

Further, since a state generated by a result when the hole density in the CuBr layer 1 decreases by doping of electrons from adsorbed ammonia molecules is an unstable state in which the electric field in the inside of the CuBr layer 1 is higher, namely, the potential is higher, in comparison with that in a state before absorption of ammonia molecules occurs, the state has a tendency that the ammonia molecules are desorbed to return to an original state. Therefore, the time required until the signal of the potential detected by the gas sensor recovers an original state when the supply of ammonia molecules stops decreases. Further, by performing the process for decreasing the hole density in the CuBr layer 1 hereinafter described, the time required until the signal of the potential detected by the gas sensor recovers an original state decreases further.

It is to be noted that, as apparent from the principle described above, if the thickness of the depletion layer formed by direct contact of the p-type semiconductor layer 1, which functions as a detection body, with the first electrode 2 is excessively small, then it is difficult for the gas sensor to operate in accordance with the principle described above. Therefore, in order to allow a thick depletion layer to form with certainty such that the gas sensor operates with certainty in accordance with the principle described above, it is preferable to perform a process for decreasing the hole concentration (hole density) in the p-type semiconductor layer 1. Here, as a process for decreasing the hole concentration in the inside of the p-type semiconductor layer 1, a process for doping a material that serves as a donor of electrons may be performed. For example, where a CuBr layer is used as the p-type semiconductor layer 1, a process may be performed by which it is contacted with reducing gas containing, for example, ammonia molecules such that ammonia molecules that serves as a donor of electrons are adsorbed to the surface thereof and then the CuBr layer is baked at a suitable temperature such that ammonia molecules are diffused into and fixed to the inside of the CuBr layer. It is to be noted that the reducing gas may be any gas if it can provide electrons to a p-type semiconductor, and, for example, hydrogen sulfide, alcohol or the like may be used. Further, for example, an n-type semiconductor material such as an electron transport material that is an n-type semiconductor material having a low carrier density can dope a small amount of electrons into the p-type semiconductor layer 1 configured from a compound of silver or copper. Therefore, by using an n-type semiconductor material such as an electron transport material as the high-resistance layer 3, the hole density in the inside of the p-type semiconductor layer 1 can be decreased. Accordingly, where an n-type semiconductor material such as an electron transport material is used as the high-resistance layer 3, the process for decreasing the hole density in the inside of the p-type semiconductor layer 1 described above may not be performed specifically. By this, a thick depletion layer is formed with certainty and the gas sensor operates with certainty in accordance with the principle described above. Further, the potential of the second electrode 4 becomes higher than the potential of the first electrode 2 and the time required until the signal of the potential detected by the gas sensor recovers its original state can be reduced.

Accordingly, with the gas sensor according to the present embodiment, there is an advantage that the power consumption can be reduced and good sensitivity can be obtained. In sort, a gas sensor having high sensitivity and low power consumption can be implemented.

Incidentally, also it is possible to configure a sensor apparatus 12 by coupling a detection unit 11 for detecting the potential difference between the first electrode 2 and the second electrode 4 of the gas sensor 10 of the embodiment described above (for example, refer to FIG. 9).

In this case, the sensor apparatus 12 according to the present embodiment includes the gas sensor 10 of the embodiment described hereinabove, and a detection unit 11 for detecting the potential difference between the first electrode 2 and the second electrode 4 of the gas sensor 10.

Here, where the gas sensor 10 of the embodiment described hereinabove is used, the detection unit 11 is coupled to the second electrode 4 of the gas sensor 10.

Further, preferably the detection unit 11 is a field effect transistor (FET) in that the sensor apparatus 12 can be scaled down and can amplify a variation of the potential difference that is an output signal from the gas sensor 10.

For example, as the field effect transistor (detection unit) 11, a field effect transistor that includes a gate electrode 13 to which a gate voltage is to be applied, a source electrode 14 and a drain electrode 15 from which current is to be extracted, an active layer (active region) 16 provided between the source electrode 14 and the drain electrode 15, and a gate insulating layer 17 provided between the gate electrode 13 and the active layer 16 or a like transistor is available. In this case, as the material for the active layer 16, for example, silicon, a metal oxide semiconductor and so forth are available. And, the second electrode 4 of the gas sensor 10 of the embodiment described above is coupled to the gate electrode 13 of the field effect transistor 11 configured in such a manner as just described.

In particular, the sensor apparatus 12 that includes the gas sensor 10 of the embodiment described above and the field effect transistor 11 may be configured as an integrated member as described below.

Figure 9:
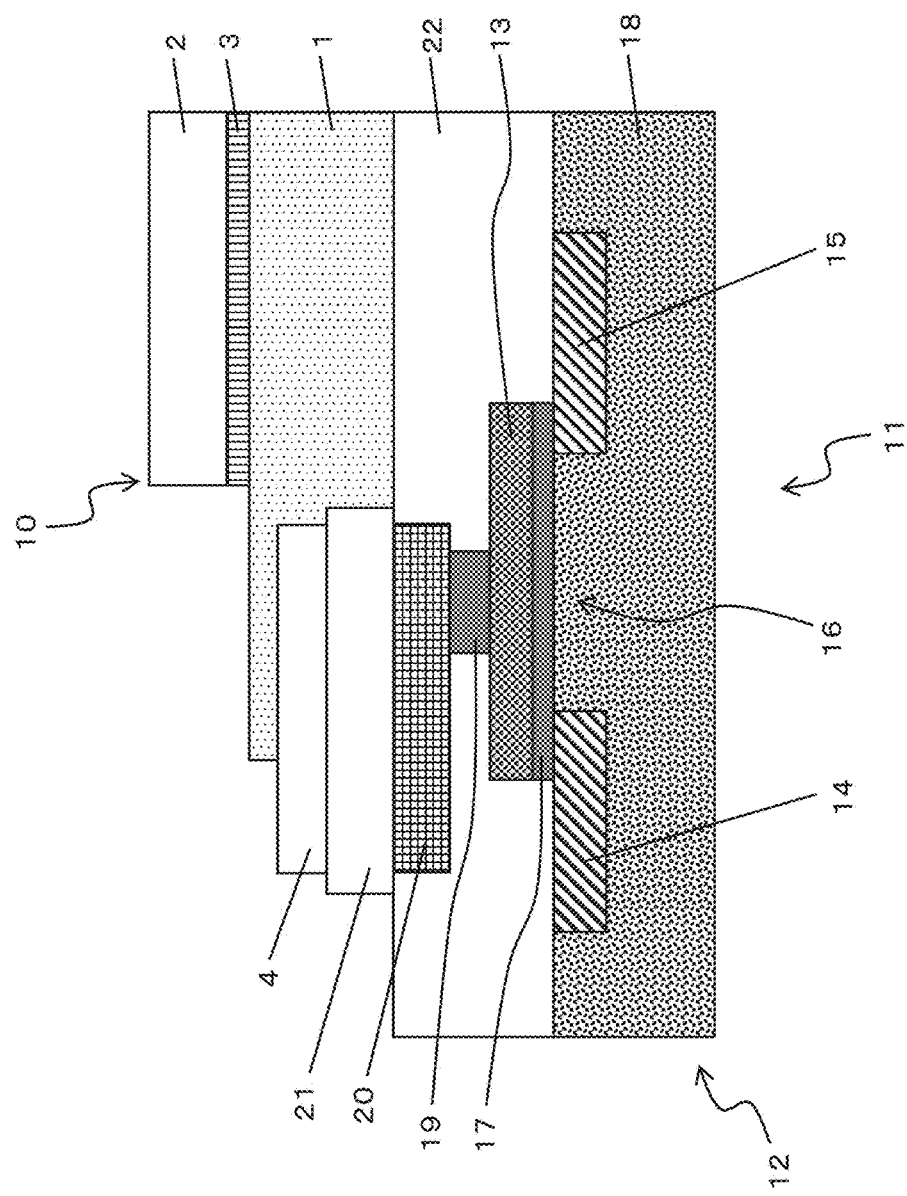
FIG. 9 is a schematic sectional view depicting an example of a configuration of a sensor apparatus that includes the gas sensor according to the embodiment.

For example, as depicted in FIG. 9, the gas sensor 10 includes a p-type semiconductor layer 1 (CuBr layer: approximately 200 nm thick), a high-resistance layer 3 (lithium fluoride layer: approximately 1.4 nm thick), a first electrode 2 (Ag electrode; approximate 80 nm thick) and a second electrode 4 (Au electrode; approximately 60 nm thick). Here, the first electrode 2 is provided at one side (here, the upper side) of the p-type semiconductor layer 1 sandwiching the high-resistance layer 3 and at a portion other than a gas contacting portion with which detection target gas is to contact. The second electrode 4 is provided at the other side (here, the lower face) of the p-type semiconductor layer 1.

The field effect transistor 11 includes a silicon substrate 18 including an active layer 16, a source electrode 14, a drain electrode 15, a gate insulating layer 17 (silicon oxide insulating layer), and a gate electrode (N-type polycrystalline silicon; N-type p-Si) (nMOS-FET). The source electrode 14 and the drain electrode 15 are provided sandwiching the active layer 16. The gate insulating layer 17 is provided between the active layer 16 and the gate electrode 13.

Further, the second electrode 4 of the gas sensor 10 and the gate electrode 13 of the field effect transistor 11 are coupled to each other through a first wiring line 19 (tungsten wiring line), a second wiring line 20 (Al—Cu—Si wiring line) and electrode pad 21 (Al pad). Further, the a insulating layer 22 (silicon oxide insulating layer) is provided so as to cover the gate insulating layer 17, gate electrode 13, first wiring line 19 and second wiring line 20, and the gas sensor 10 is provided on the insulating layer 22.

EXAMPLES

In the following, the embodiment is described in more detail in connection with examples. The present invention is not limited by the following examples.

Example 1

In the example 1, a gold electrode of approximately 6 mm wide, approximately 20 mm long and approximately 60 nm thick was formed as the second electrode by vacuum deposition on a silicon wafer (silicon substrate) 6 having a length of approximately 50 mm and a width of approximately 10 mm and having a thermal oxide film ($SiO_2$ film) 5 of a thickness of approximately 100 nm at the surface thereof, and on the gold electrode, a cuprous bromide (CuBr) layer of approximately 200 nm thick as the p-type semiconductor layer 1 was formed by sputtering using a mask so as to have a shape of approximately 8 mm wide, approximately 30 mm long and approximately 60 nm thick (refer to FIG. 2).

Then, the wafer was taken out into the atmosphere and an exposure process for approximately 10 minutes was performed. Since the atmosphere exposure causes water vapor in the atmosphere to be adsorbed to the surface of the CuBr layer 1 thereby to cause crystal of the CuBr layer 1 to grow unevenly, the surface of the CuBr layer 1 was roughened moderately.

Thereafter, a film of lithium fluoride (LiF) that is an insulating material of approximately 1.4 nm thick was formed as an insulating layer 3X (high-resistance layer 3) by vacuum deposition, and then a silver electrode of approximately 80 nm thick was formed as the first electrode 2 by vacuum deposition to produce a sensor device (gas sensor) (refer to FIG. 2).

Here, the plane size of the insulating layer 3X and the first electrode 2, namely, the plane size of the stacked film of LiF and silver, was approximately 10 mm wide and approximately 20 mm long, and the gap length (indicated by reference character g in FIG. 2) that is the distance between an end of the first electrode 2 and an end of the second electrode 4, was approximately 0.5 mm.

A result when the stacked state of the CuBr layer 1, LiF layer 3X and silver electrode 2 of the sensor device produced in such a manner as described above was observed using a transmission electron microscope (TEM: Transmission Electron Microscope) is depicted in FIG. 10.

Figure 10:
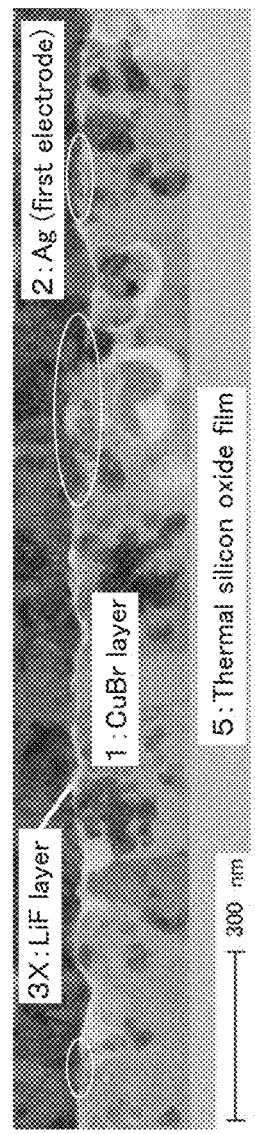
FIG. 10 is a view depicting a transmission electron microscope image of an interface configured from the first electrode formed from silver, an insulating layer formed from lithium fluoride and a p-type semiconductor layer formed from cuprous bromide in a sensor device in an example 1.

As depicted in FIG. 10, it can be recognized that the LiF layer 3X is interrupted in each region surrounded by a white round mark and a direct contact region of the CuBr layer 1 and the silver electrode 2 is formed in the region. Further, the contrast that can be seen in the CuBr layer 1 arises from uneven crystal growth of the CuBr layer 1 caused by contact with water vapor.

Thereafter, the 196 system DMM by Keighley was coupled to the sensor device produced in such a manner as described such that the second electrode 4 serves as a detection electrode (action electrode) and the first electrode 2 serves as a reference electrode so as to make it possible to measure the potential difference between the electrodes.

Figure 11:
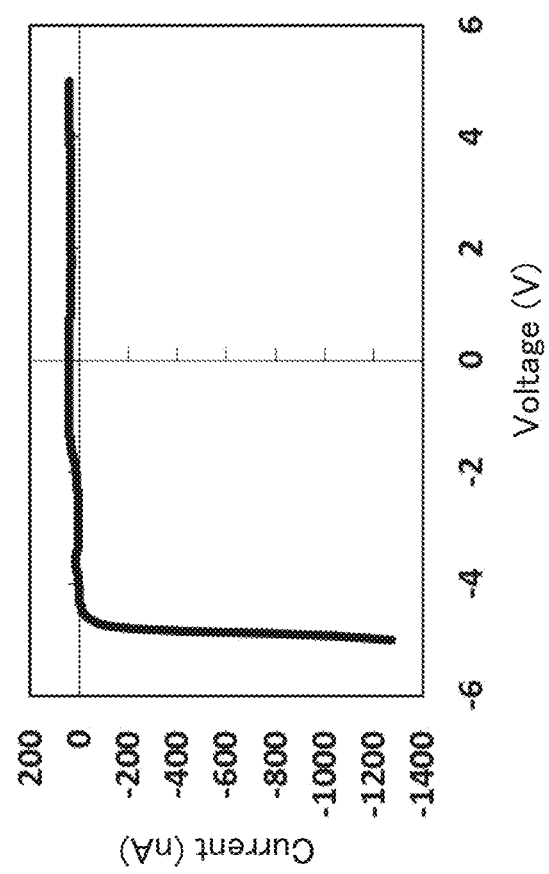
FIG. 11 is a view depicting an I-V curve in pure nitrogen of the sensor device of the example 1.

Here, FIG. 11 depicts an I-V curve measured in pure nitrogen at a room temperature (approximately 23° C.). It is to be noted that the measurement of the sweep of the action electrode 4 was performed in the direction from negative to positive.

As depicted in FIG. 11, it is recognized that an electricity accumulation action is observed at an initial stage of the measurement and the sensor device is in a substantially insulating state in that the electric resistance is extremely high. It is to be noted that the in-plane resistance in pure nitrogen through the gap of approximately 0.5 mm of the CuBr layer 1 used here is fixed within a range of ±5 V and is approximately 20 kΩ. Accordingly, almost all of the device resistance described above arises from the state in the proximity of the interface configured from the CuBr layer 1 and the silver electrode 2 and LiF layer 3X. In other words, since a depletion layer is formed in the inside of the CuBr layer 1 that contacts directly with the silver electrode 2, even if a large number of detects exist in the LiF layer 3X, within a voltage range of ±5 V, the resistance is extremely high and it can be recognized that operation as a capacitor is obtained.

Thereafter, the sensor device was placed into a nitrogen gas flow path of a flow rate of 4 L/min, and the gas source was switched between pure nitrogen and nitrogen containing ammonia of a concentration of approximately 1 ppm at a room temperature (approximately 23° C.) to evaluate a reaction of the sensor device to ammonia.

Figure 12:
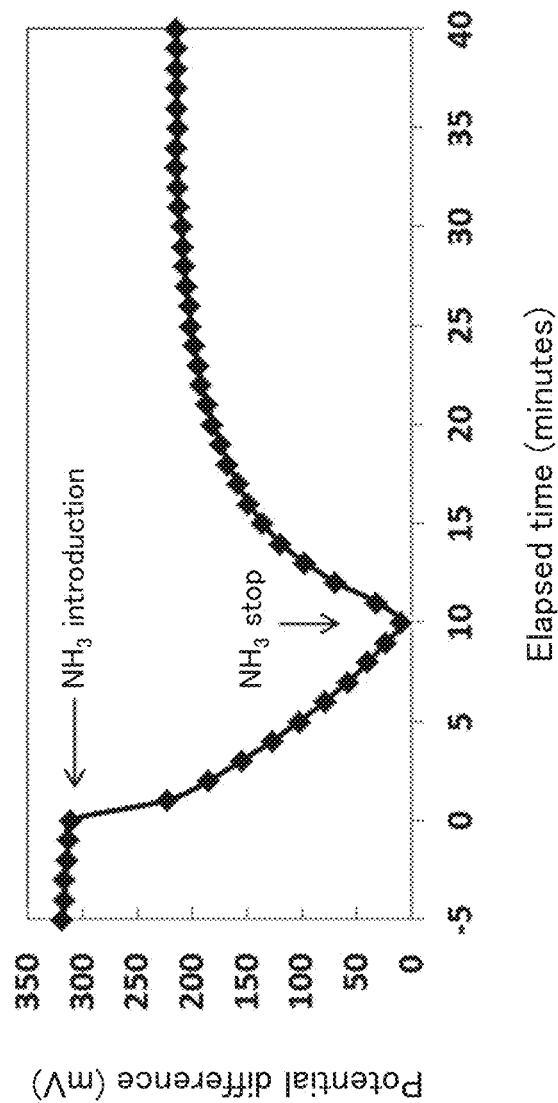
FIG. 12 is a view depicting a variation of a potential difference between electrodes in the case where the sensor device of the example 1 is exposed to nitrogen flow that contains ammonia of a concentration of approximately 1 ppm.

FIG. 12 indicates a time variation of the reaction (response) of the measured potential difference between the first electrode 2 and the second electrode 4 to ammonia.

As depicted in FIG. 12, it can be recognized that, when the gas flow is switched from pure nitrogen to nitrogen containing ammonia of the concentration of approximately 1 ppm, the potential of the second electrode 4 that serves as a detection electrode relatively drops by approximately 300 mV and a high sensitivity is obtained. Further, when the gas flow was switched back to pure nitrogen, the potential recovered.

By configuring the sensor device such that it includes a p-type semiconductor layer 1 (here, CuBr) that contains copper and is to contact with detection target gas (here, ammonia), a first electrode 2 (here, an Ag electrode) service as a Schottky electrode to the p-type semiconductor layer 1, a second electrode 4 (here, an Au electrode) serving as an ohmic electrode to the p-type semiconductor layer 1, and an insulating layer 3X (here, a lithium fluoride layer) as the high-resistance layer 3 provided between the p-type semiconductor layer 1 and the first electrode 2 such that the p-type semiconductor layer 1 and the first electrode 2 partly contact with each other therethrough and having a resistance higher than those of the p-type semiconductor layer 1 and the first electrode 2, that, in the coupling region between the p-type semiconductor layer 1 and the first electrode 2, a region in which the p-type semiconductor layer 1 and the first electrode 2 are coupled directly to each other and another region in which the insulating layer 3X exists between the p-type semiconductor layer 1 and the first electrode 2 exist in a mixed manner, that a gap g is provided between the first electrode 2 and the second electrode 4, and that gas that is an observation target contacts with the surface of the p-type semiconductor layer 1 in the proximity of the second electrode 4 as described above, a gas sensor of the potential difference measurement type having a high sensitivity was implemented successfully.

Example 2

In the example 2, upon production of the sensor device configured in such a manner as in the example 1, a process for decreasing the hole concentration (hole density) in the inside of the CuBr layer as the p-type semiconductor layer 1 was performed. It is to be noted that a sensor device was produced by the same method and conditions as those in the example 1 except the process for decreasing the hole concentration.

Here, as the process for decreasing the hole concentration in the inside of the CuBr layer 1, after sputtering film formation and atmosphere exposure of the CuBr layer 1, a process for adsorbing ammonia molecules to the surface of the CuBr layer 1 and baking the CuBr layer 1 to dope ammonia molecules into the inside of the CuBr layer 1 was performed.

In particular, after a CuBr layer 1 of approximately 200 nm thick was formed by sputtering and atmosphere exposure for approximately 10 minutes was performed, the CuBr layer 1 was immersed for approximately minutes in 2-propanol that contains ammonia by approximately 20 ppm by weight, whereafter drying was performed for approximately 10 minutes at approximately 60° C. in a nitrogen atmosphere to dope ammonia molecules into the inside of the CuBr layer 1.

A result when the stacked state of the CuBr layer 1, LiF layer 3X and silver electrode 2 of the sensor device produced in such a manner as described above was observed using a transmission electron microscope (TEM: Transmission Electron Microscope) is depicted in FIG. 13.

Figure 13:
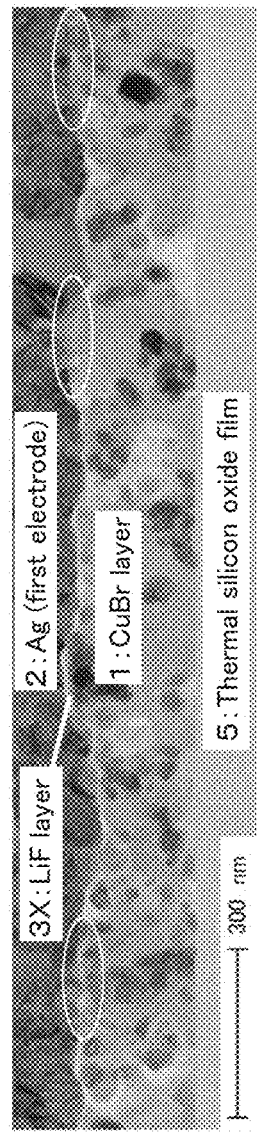
FIG. 13 is a view depicting a transmission electron microscope image of an interface configured from a first electrode formed from silver, an insulating layer (high-resistance layer) formed from lithium fluoride and a p-type semiconductor layer formed from cuprous bromide in a sensor device of an example 2.

As depicted in FIG. 13, it can be recognized that the LiF layer 3X is interrupted in each region surrounded by a white round mark and a direct contact region of the CuBr layer 1 and the silver electrode 2 is formed in the region similarly as in the case of the example 1.

Thereafter, the 196 system DMM by Keighley was coupled to the sensor device produced in such a manner as described such that the second electrode 4 serves as a detection electrode (action electrode) and the first electrode 2 serves as a reference electrode so as to make it possible to measure the potential difference between the electrodes.

Figure 14:
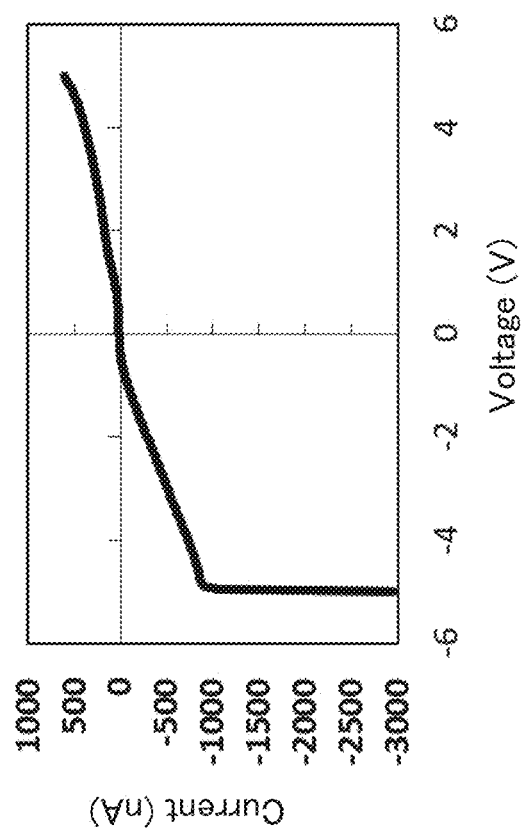
FIG. 14 is a view depicting an I-V curve in pure nitrogen of the sensor device of the example 2.

Here, FIG. 14 depicts an I-V curve measured in pure nitrogen at a room temperature (approximately 23° C.). It is to be noted that the measurement of the sweep of the action electrode 4 was performed in the direction from negative to positive.

As depicted in FIG. 14, it is recognized that, since an electricity accumulation action is observed at an initial stage of the measurement, the present device has a nature as a capacitor, that, since the resistance value in the proximity of a bias voltage of approximately 0 V is approximately 50 MΩ and is not extremely high and, although the IV curve is a curve like that of a semiconductor, no notable rise in current is observed, the present device has a parallel configuration of a capacitor and a Schottky junction, and that, although the CuBr layer 1 and the silver electrode 2 form a Schottky junction, the barrier is low. It is to be noted that the in-plane resistance in pure nitrogen through the gap g of approximately 0.5 mm of the CuBr layer 1 used here is fixed within a range of ±5 V and is approximately 12 kΩ. Accordingly, almost all of the device resistance described above originates from the state in the proximity of the interface configured from the CuBr layer 1 and the silver electrode 2 and insulating layer 3X.

Thereafter, the sensor device was placed into a nitrogen gas flow path of a flow rate of 4 L/min, and the gas source was switched between pure nitrogen and nitrogen containing ammonia of a concentration of approximately 1 ppm at a room temperature (approximately 23° C.) to evaluate a reaction of the sensor device to ammonia.

Figure 15:
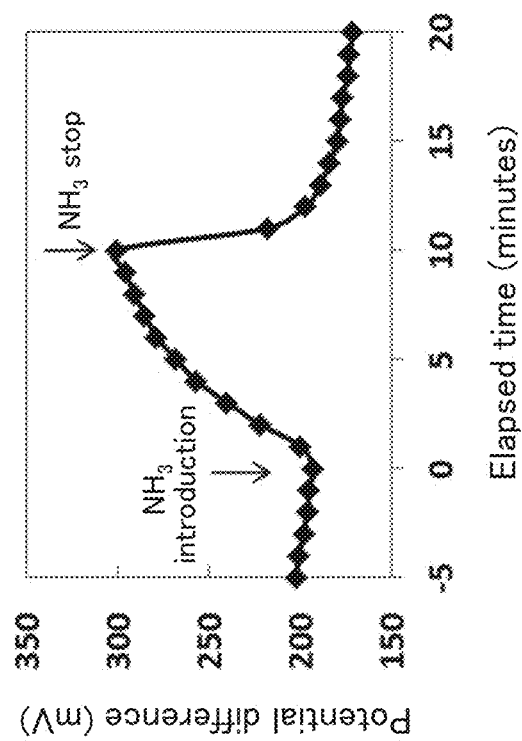
FIG. 15 is a view depicting a variation of a potential difference between electrodes in the case where the sensor device of the example 2 is exposed in nitrogen flow that contains ammonia of a concentration of approximately 1 ppm.

FIG. 15 indicates a time variation of the reaction of the potential difference between the first electrode 2 and the second electrode 4 to ammonia measured by a method similar to that in the example 1.

As depicted in FIG. 15, when the gas flow was switched from pure nitrogen to nitrogen containing ammonia of the concentration of approximately 1 ppm, the potential of the second electrode 4 that serves as a detection electrode rises by approximately 100 mV with respect to the potential of the first electrode 2 that is a reference electrode, but when the gas flow was switched to pure nitrogen, the potential recovered in approximately five minutes. In this manner, where the example 2 is compared with the example 1, it can be recognized that, although the response strength drops, the speed at which the potential recovers is much faster.

It can be recognized that, by setting the hole density (carrier density) in the inside of the p-type semiconductor layer 1 to a suitable range as in the case of the sensor device of the example 2 in this manner, the recovery speed after contact with observation target gas comes to an end can be increased significantly.

Comparative Example 1

In the comparative example 1, a sensor device was produced without providing a LiF layer as the insulating layer 3X between a CuBr layer as the p-type semiconductor layer 1 and a silver electrode as the first electrode 2. In other words, in the comparative example 1, a sensor device was produced similarly as in the example 1 except that a LiF layer as the insulating layer 3X was not provided. Further, in the comparative example 1, a sensor device was produced without performing the hole concentration reduction process of the example 2 after spluttering film formation and atmosphere exposure of the CuBr layer 1. It is to be noted that the other production conditions are same as those in the example 1.

The 196 system DMM by Keighley was coupled to the sensor device produced in such a manner as described such that the second electrode 4 serves as a detection electrode (action electrode) and the first electrode 2 serves as a reference electrode so as to make it possible to measure the potential difference between the electrodes.

Figure 16:
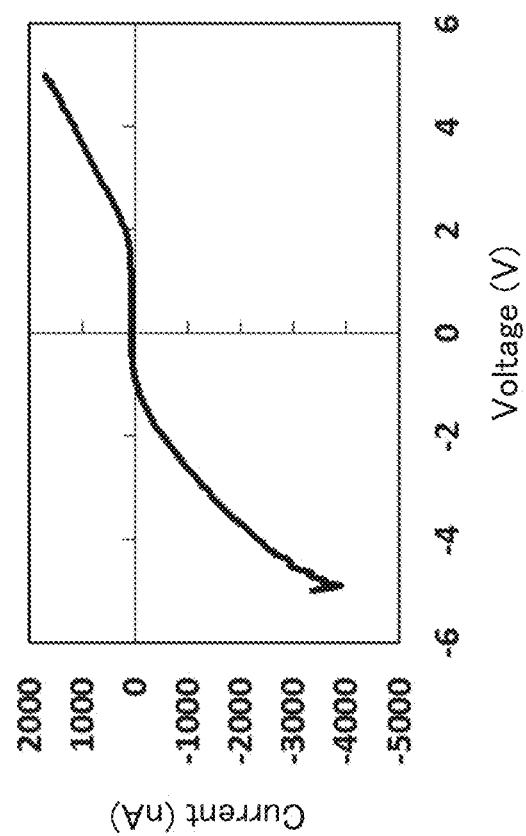
FIG. 16 is a view depicting an I-V curve in pure nitrogen of a sensor device of a comparative example 1.

Here, FIG. 16 depicts an I-V curve measured in pure nitrogen at a room temperature (approximately 23° C.). It is to be noted that the measurement of the sweep of the second electrode 4 was performed in the direction from negative to positive.

As depicted in FIG. 16, it is recognized that, since the resistance value of the present device in the proximity of 0 V is approximately 150 MΩ and besides a clear current rise is observed, a Schottky junction having a clear barrier is formed on the interface between the CuBr layer 1 and the silver electrode 2. Where such a Schottky junction as just described is formed, a rectification performance by the Schottky barrier exists, and since it is difficult for electrons doped in the CuBr layer 1 to flow out into the silver electrode 2, the present device exhibits a response to ammonia.

Figure 17:
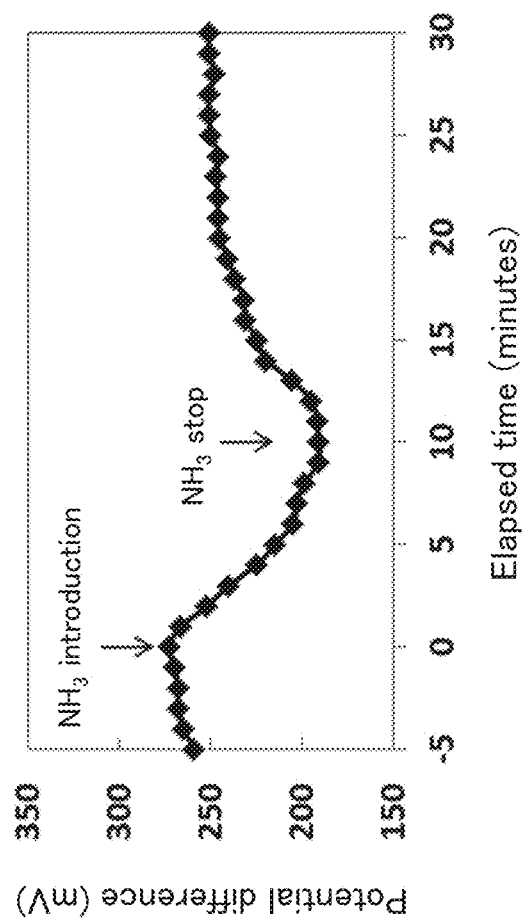
FIG. 17 is a view depicting a variation of a potential difference between electrodes in the case where the sensor device of the comparative example 1 is exposed in nitrogen flow that contains ammonia of a concentration of approximately 1 ppm.

FIG. 17 depicts a time variation of the response of the potential difference between the first electrode 2 and the second electrode 4 measured by a method similar to that in the example 1 to ammonia.

As depicted in FIG. 17, when the gas flow was switched from pure nitrogen to nitrogen containing ammonia of a concentration of approximately 1 ppm, the variation width of the potential difference between the potential of the second electrode 4 that is a detection electrode and the potential of the first electrode 2 that is a reference electrode was approximately 80 mV, and the recovery after nitrogen containing ammonia was stopped and the gas flow was switched to pure nitrogen was very slow. In this manner, in the configuration of the present device, since electrodes doped from ammonia are stored into the depletion layer in the proximity of the interface between the CuBr layer 1 and the silver electrode 2, the distance to the positive charge in the inside of the first electrode 2, which is to be paired with the electrons, is small and movement (dedoping) of electrons to ammonia required for dedoping of ammonia from the surface of the CuBr layer 1 is difficult, the recovery became slow. Further, since no insulating layer exists between the CuBr layer 1 and the silver electrode 2, the distance between the electrons and the positive charge across the interface between them decreases, and as a result, since the electrostatic capacitance at the location increases, the potential difference between the electrodes appearing when an equal number of electrons are accumulated decreases. It can be recognized that, where an insulating layer is not provided between the CuBr layer 1 and the silver electrode 2, a desirable result as in the example 1 is not obtained in this manner.

Example 3

In the example 3, in place of the insulating layer 3X (lithium fluoride that is an insulating material) provided in the sensor device of the example 1, an electron transport layer (n-type semiconductor layer having a work function smaller than those of the p-type semiconductor layer 1 and the first electrode 2) 3Y was formed by forming a layer of bathocuproin (BCP), which is an electron transport material of approximately 6 nm thick, by vacuum deposition as the high-resistance layer 3 to produce a sensor device similarly as in the example 1 (for example, refer to FIG. 3). However, the thickness of the CuBr film as the p-type semiconductor layer 1 was approximately 400 nm.

A dark field image obtained by observing the stacked state of the CuBr layer 1, BCP layer 3Y and silver electrode 2 of the sensor device produced in this manner using a scanning transmission electron microscope (STEM; Scanning Transmission Electron Microscope) is depicted in FIG. 18.

Figure 18:
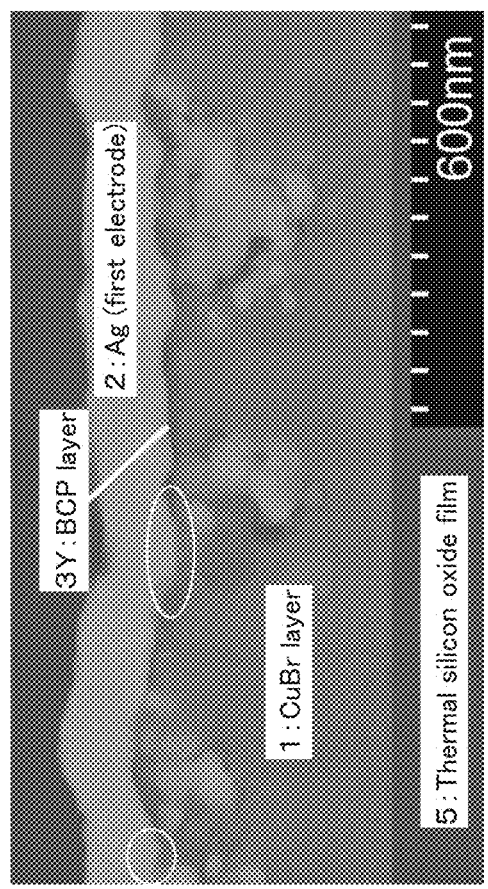
FIG. 18 is a view depicting a scanning transmission electron microscope image (bright field image) of an interface configured from a first electrode formed from silver, an electron transport layer (n-type semiconductor layer; high-resistance layer) formed from bathocuproin and a p-type semiconductor layer formed from cuprous bromide in a sensor device of an example 3.

In FIG. 18, what looks as a thin line between the CuBr layer 1 and the silver electrode 2 is the BCP layer 3Y, and it can be recognized that the BCP layer 3Y is interrupted in each region surrounded by a white round mark due to the surface roughness of the CuBr layer 1 such that a direct contact region between the CuBr layer 1 and the silver electrode 2 is formed. Further, although some contrast appears in the CuBr layer 1, this arises from uneven crystal growth of the CuBr layer generated by contact with water vapor.

Thereafter, the 196 system DMM by Keighley was coupled to the sensor device produced in such a manner as described such that the second electrode 4 serves as a detection electrode (action electrode) and the first electrode 2 serves as a reference electrode so as to make it possible to measure the potential difference between the electrodes.

Figure 19:
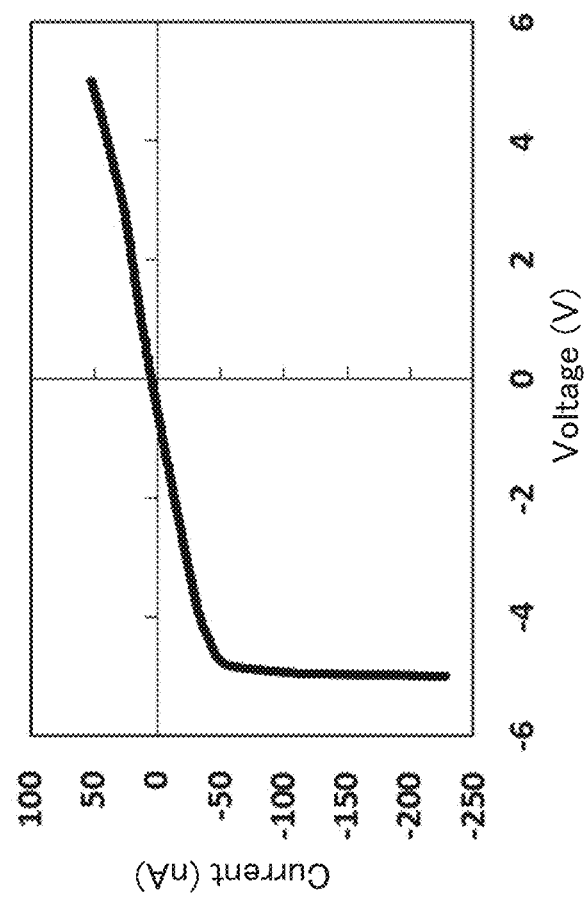
FIG. 19 is a view depicting an I-V curve in pure nitrogen of the sensor device of the example 3.

Here, FIG. 19 depicts an I-V curve measured in pure nitrogen at a room temperature (approximately 23° C.). It is to be noted that the measurement of the sweep of the action electrode 4 was performed in the direction from negative to positive.

As depicted in FIG. 19, it is recognized that, since an electricity accumulation action is observed at an initial stage of the measurement, the present device has a nature as a capacitor, that, since the resistance value in the proximity of a bias voltage of approximately 0 V is approximately 100 MΩ and, although no notable rise of current can be observed, the IV curve is a curve like that of a semiconductor, the present device has a parallel configuration of a capacitor and a Schottky junction, and that, although the CuBr layer 1 and the silver electrode 2 form a Schottky junction, the barrier is low.

Since the CuBr layer 1 used here has a thickness doubled from that of the CuBr layer 1 in the example 1, the reason why, although the resistance in the in-plane direction (film in-plane direction) is lower than that in the example 1, the IV curve is closer to that in the example 2 than that in the example 1 is that, since the BCP layer 3Y coordinates to the cation of copper and has ability to donate electrons, electrons are doped into the CuBr layer 1 and the hole concentration remains decreased. In short, to use the BCP layer 3Y is an alternative to the hole concentration decreasing process (ammonia doping process) in the example 2.

Thereafter, the sensor device was placed into a nitrogen gas flow path of a flow rate of 4 L/min, and the gas source was switched between pure nitrogen and nitrogen containing ammonia of a concentration of approximately 1 ppm at a room temperature (approximately 23° C.) to evaluate a reaction of the sensor device to ammonia.

Figure 20:
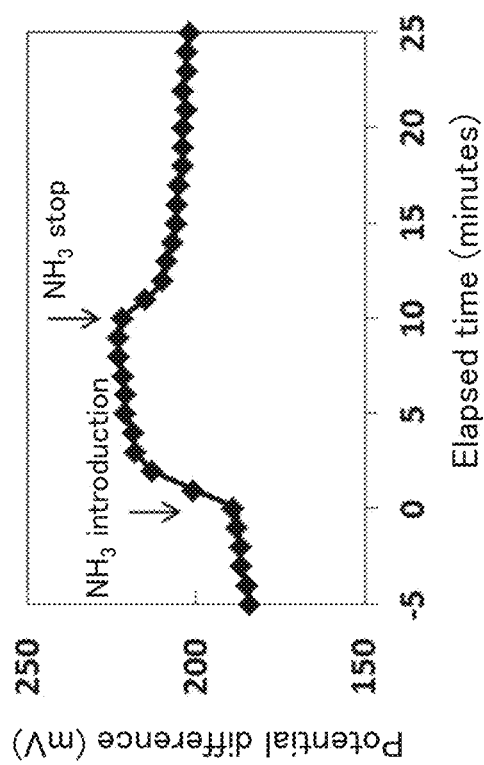
FIG. 20 is a view depicting a variation of a potential difference between electrodes in the case where the sensor device of the example 3 is exposed in nitrogen flow that contains ammonia of a concentration of approximately 1 ppm.

FIG. 20 indicates a time variation of the reaction of the potential difference between the first electrode 2 and the second electrode 4 to ammonia measured by a method similar to that in the example 1.

As depicted in FIG. 20, when the gas flow was switched from pure nitrogen to nitrogen containing ammonia of a concentration of approximately 1 ppm, the potential of the second electrode 4 that serves as a detection electrode rises by approximately 30 mV with respect to the potential of the first electrode 2 that is a reference electrode, and when the gas flow was switched to pure nitrogen, the potential recovered in approximately 10 minutes.

By configuring the sensor device such that it includes a p-type semiconductor layer 1 (here, CuBr) that contains copper and is to contact with detection target gas (here, ammonia), a first electrode 2 (here, an Ag electrode) serving as a Schottky electrode to the p-type semiconductor layer 1, a second electrode 4 (here, an Au electrode) serving as an ohmic electrode to the p-type semiconductor layer 1, and a high-resistance layer 3 (here, an n-type semiconductor layer 3Y having a work function lower than those of the p-type semiconductor layer and the first electrode; here, a BCP layer) provided between the p-type semiconductor layer 1 and the first electrode 2 such that the p-type semiconductor layer 1 and the first electrode 2 partly contact with each other therethrough and having a resistance higher than those of the p-type semiconductor layer 1 and the first electrode 2, that, in the coupling region between the p-type semiconductor layer 1 and the first electrode 2, a region in which the p-type semiconductor layer 1 and the first electrode 2 are coupled directly to each other and another region in which the high-resistance layer 3 exists between the p-type semiconductor layer 1 and the first electrode 2 exist in a mixed manner, that a gap is provided between the first electrode 2 and the second electrode 4, and that gas that is an observation target contacts with the surface of the p-type semiconductor layer 1 in the proximity of the second electrode 4 as described above, a gas sensor of the potential difference measurement type having a high sensitivity was implemented successfully and the recovery speed after the contact with observation target gas comes to an end was increased successfully.

Comparative Example 2

In the comparative example 2, a sensor device was produced by a method and conditions similar to those in the example 3 except that atmosphere exposure was not performed after film formation of the CuBr layer 1 and that the thickness of the BCP layer 3Y was 4 nm.

A dark field image obtained by observing the stacked state of the CuBr layer 1, BCP layer 3Y and silver electrode 2 of the sensor device produced in this manner using a scanning transmission electron microscope (STEM; Scanning Transmission Electron Microscope) is depicted in FIG. 21.

Figure 21:
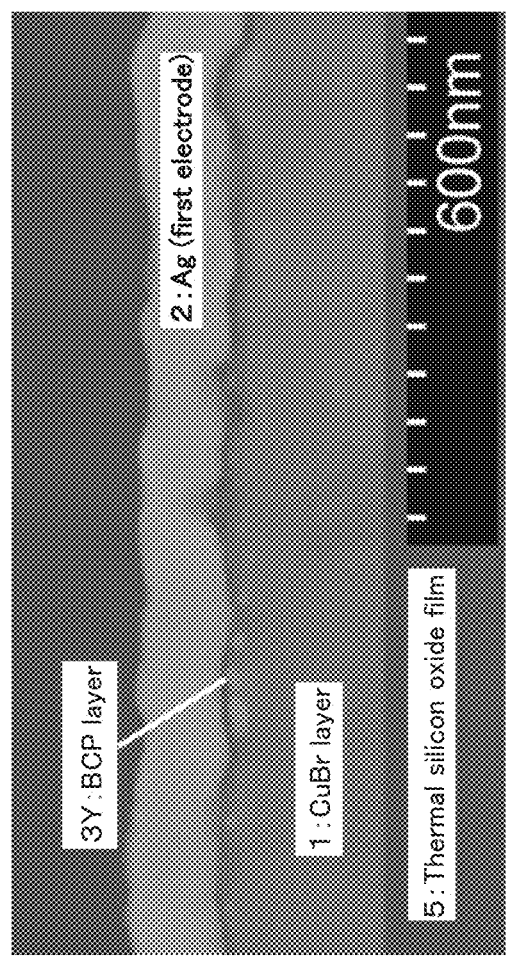
FIG. 21 is a view depicting a scanning transmission electron microscope image (bright field image) of an interface configured from a first electrode formed from silver, an electron transport layer (n-type semiconductor layer; high-resistance layer) formed from bathocuproin and a p-type semiconductor layer formed from cuprous bromide in a sensor device of a comparative example 2.

As depicted in FIG. 21, since atmosphere exposure was not performed, not only uneven crystal grow appearing in the CuBr layer 1 but also the surface roughness of the CuBr layer 1 are much smaller in comparison with those in the case of the example 3 (refer to FIG. 18). Further, a location at which the BCP layer 3Y is interrupted, namely, a direct contact region between the CuBr layer 1 and the silver electrode 2, is not observed at least clearly.

Thereafter, the 196 system DMM by Keighley was coupled to the sensor device produced in such a manner as described such that the second electrode 4 serves as a detection electrode (action electrode) and the first electrode 2 serves as a reference electrode so as to make it possible to measure the potential difference between the electrodes.

Figure 22:
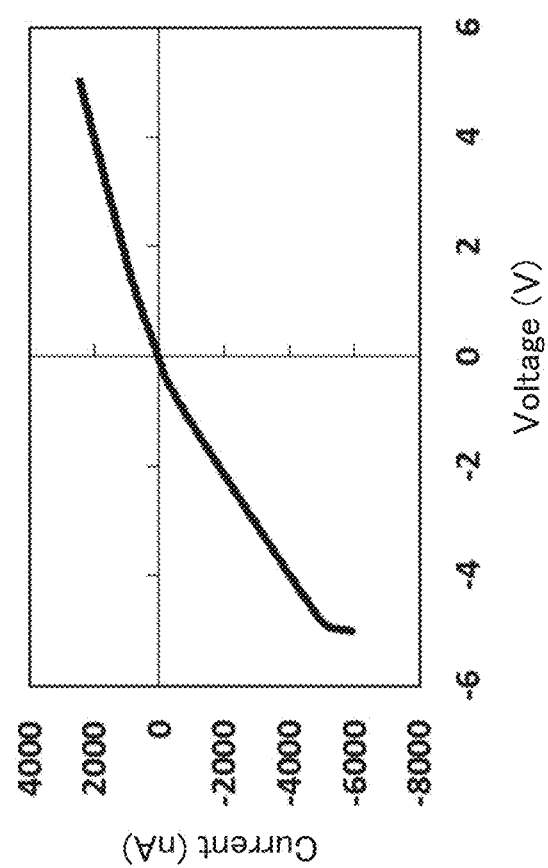
FIG. 22 is a view depicting an I-V curve in pure nitrogen of the sensor device of the comparative example 2.

Here, FIG. 22 depicts an I-V curve measured in pure nitrogen at a room temperature (approximately 23° C.). It is to be noted that the measurement of the sweep of the action electrode 4 was performed in the direction from negative to positive.

As depicted in FIG. 22, an electricity accumulation action is observed at an initial stage of the measurement and the potential of the second electrode 4 that serves as an action electrode varies substantially linearly in each of the negative region and the positive region, and while the resistance in the negative region is approximately 1.2 MΩ, the resistance in the positive region is approximately 1.6 MΩ. The difference in resistance value by the sign of the potential of the second electrode 4 as an action electrode arises from the fact that a small amount of electrons doped from the BCP layer 3Y, which is an n-type semiconductor and has a low carrier concentration, into the CuBr layer 1 causes a very low built-in voltage in the inside of the CuBr layer 1 near to the interface with the BCP layer 3Y, and except this effect, the present device can be considered a capacitor that exhibits leak by tunneling. In particular, since, in the comparative example 2, atmosphere exposure is not performed after formation of the CuBr layer 1, the surface roughness of the CuBr layer 1 is low in comparison with that in the example 3, and a location at which the BCP layer 3Y is interrupted, namely, a direct contact region between the CuBr layer 1 and the silver electrode 2, is reduced to such a degree that it can be ignored. This results in tunnel junction between the CuBr layer 1 and the silver electrode 2.

Thereafter, the sensor device was placed into a nitrogen gas flow path of a flow rate of 4 L/min, and the gas source was switched between pure nitrogen and nitrogen containing ammonia of a concentration of approximately 1 ppm at a room temperature (approximately 23° C.) to evaluate a reaction of the sensor device to ammonia.

Figure 23:
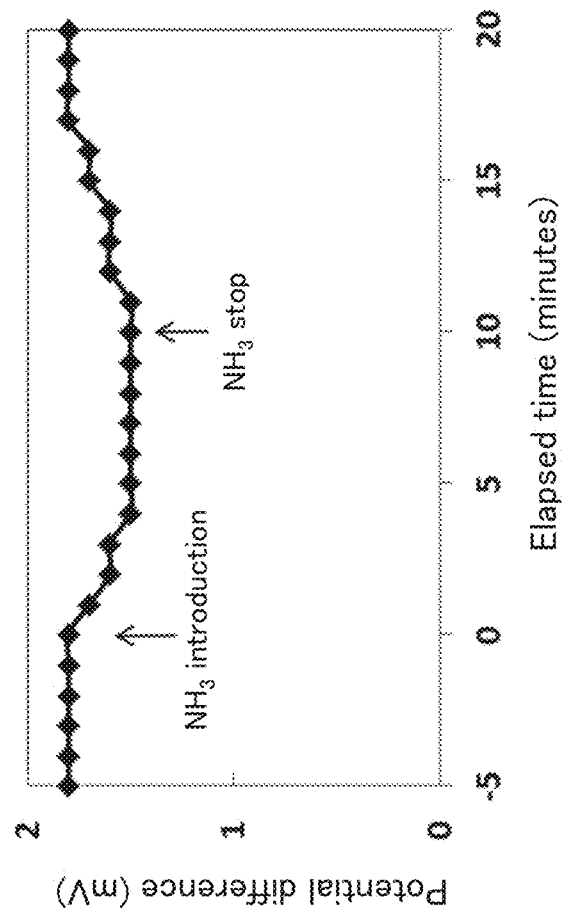
FIG. 23 is a view depicting a variation of a potential difference between electrodes in the case where the sensor device of the comparative example 2 is exposed in pure nitrogen that contains ammonia of a concentration of approximately 1 ppm.

FIG. 23 indicates a time variation of the reaction of the potential difference between the first electrode 2 and the second electrode 4 to ammonia measured by a method similar to that in the example 3.

As depicted in FIG. 23, in comparison with the example 3, the variation amount of the potential difference is approximately 0.4 mV and is much smaller reflecting that the internal resistance of the device is lower by two digits.

In this manner, it can be recognized that a gas sensor of the potential difference measurement type having high sensitivity can be implemented by performing atmosphere exposure after formation of the CuBr layer 1 to suitably increase the surface roughness of the CuBr layer 1 such that the BCP layer 3Y is interrupted to form a direct contact region between the CuBr layer 1 and the silver electrode 2 as in the example 3, namely, by providing the BCP layer 3Y (high-resistance layer 3) having a resistance higher than those of the CuBr layer 1 and the silver electrode 2 such that it is provided between the silver electrode (first electrode) 2 serving as a Schottky electrode and the CuBr layer (p-type semiconductor layer) 1 so as to allow the silver electrode 2 and the CuBr layer 1 to partly contact with each other therethrough.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A gas sensor, comprising:
   a p-type semiconductor layer that contains copper or silver cations and contacts with detection target gas;
   a first electrode that is a Schottky electrode to the p-type semiconductor layer;
   a high-resistance layer that is provided between the p-type semiconductor layer and the first electrode and has resistance higher than that of each of the p-type semiconductor layer and the first electrode; and a second electrode that is an ohmic electrode to the p-type semiconductor layer,
   wherein the high-resistance layer has intermittent defects through which the first electrode directly contacts the p-type semiconductor layer.

2. The gas sensor according to claim 1, wherein the p-type semiconductor layer and the first electrode are coupled such that a capacitor and Schottky junction are parallel to each other.

3. The gas sensor according to claim 1, wherein the high-resistance layer is an insulating layer.

4. The gas sensor according to claim 1, wherein the high-resistance layer is an n-type semiconductor layer having a work function lower than those of the p-type semiconductor layer and the first electrode.

5. The gas sensor according to claim 1, wherein, when reducing detection target gas contacts with the p-type semiconductor layer, a potential of the second electrode varies in a positive direction.

6. The gas sensor according to claim 1, wherein the p-type semiconductor layer contains one selected from a group consisting of cuprous bromide, cuprous oxide, silver bromide and silver sulfide.

7. A sensor apparatus, comprising:
   the gas sensor according to claim 1; and
   a detection unit that is coupled to the gas sensor and detects a potential difference between the first electrode and the second electrode of the gas sensor.

8. The sensor apparatus according to claim 7, wherein the detection unit is a field effect transistor.

9. A gas sensor, comprising:
a p-type semiconductor layer that contains copper or silver cations and contacts with detection target gas;
a first electrode that is a Schottky electrode to the p-type semiconductor layer;
a high-resistance layer that is provided between the p-type semiconductor layer and the first electrode such that the p-type semiconductor layer and the first electrode partly contact with each other and has resistance higher than that of each of the p-type semiconductor layer and the first electrode; and
a second electrode that is an ohmic electrode to the p-type semiconductor layer,
wherein the first electrode and the second electrode contain a metal material having an ionization tendency lower than that of a metal element contained in the p-type semiconductor layer.

* * * * *